United States Patent

Naud et al.

(10) Patent No.: US 6,570,022 B2
(45) Date of Patent: May 27, 2003

(54) PREPARATION OF BIS-(1(2)H-TETRAZOL-5-YL)-AMINE MONOHYDRATE

(75) Inventors: Darren L. Naud, Los Alamos, NM (US); Michael A. Hiskey, Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/957,938

(22) Filed: Sep. 21, 2001

(65) Prior Publication Data

US 2003/0060634 A1 Mar. 27, 2003

(51) Int. Cl.⁷ .............................................. C07D 403/12
(52) U.S. Cl. ...................................................... 548/251
(58) Field of Search ................................. 548/251, 250

(56) References Cited

U.S. PATENT DOCUMENTS 5,468,866 A * 11/1995 Highsmith et al. .......... 548/251
6,040,453 A * 3/2000 Hyoda et al. ............... 548/250

FOREIGN PATENT DOCUMENTS

WO        95/18802    * 7/1995

* cited by examiner

Primary Examiner—Joseph K. McKane
Assistant Examiner—Golam M. M. Shameem
(74) Attorney, Agent, or Firm—Bruce H. Cottrell

(57) ABSTRACT

A process of preparing bis-(1(2)H-tetrazol-5-yl)-amine monohydrate is provided including combining a dicyanamide salt, an azide salt and water to form a first reaction mixture, adding a solution of a first strong acid characterized as having a pKa of less than about 1 to said first reaction mixture over a period of time characterized as providing a controlled reaction rate so as to gradually form hydrazoic acid without loss of significant quantities of hydrazoic acid from the solution while heating the first reaction mixture at temperatures greater than about 65° C., heating the resultant reaction mixture at temperatures greater than about 65° C. for a period of time sufficient to substantially completely form a reaction product, treating the reaction product with a solution of a second strong acid to form a product of bis-(1(2)H-tetrazol-5-yl)-amine monohydrate, and, recovering the bis-(1(2)H-tetrazol-5-yl)-amine monohydrate product.

12 Claims, No Drawings

PREPARATION OF BIS-(1(2)H-TETRAZOL-5-YL)-AMINE MONOHYDRATE

This invention was made with government support under Contract No. W-7405-ENG-36 awarded by the U.S. Department of Energy. The government has certain rights in the invention.

FIELD OF THE INVENTION

The present invention relates generally to the preparation of bis-(1(2)H-tetrazol-5-yl)-amine monohydrate (known as BTAw).

BACKGROUND OF THE INVENTION

A method of synthesizing bis-(1(2)H-tetrazol-5-yl)-amine is described by William Norris et al., "Cyanoguanyl Azide Chemistry," Journal of the American Chemical Society, pp. 650–660, March 1964, which is incorporated herein by reference. Their compound was actually bis-(1(2)H-tetrazol-5-yl)-amine monohydrate (BTAw) with the following structure:

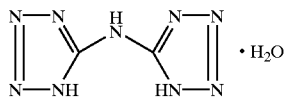

The BTAw synthesis method described by Norris et al. reacts sodium dicyanamide, sodium azide, and a trimethylammonium chloride catalyst in 100 milliliters (ml) of water at a reflux temperature for about one day. The process of Norris et al. has several disadvantages. For instance, the catalyst used by Norris et al. is expensive and unavailable on a large scale. Furthermore, the tertiary alkyl amine formed in the reaction process has a pungent, obnoxious odor. Another disadvantage of the Norris et al. process is the use of excess sodium azide, which represents a safety and disposal concern. In addition, the process of Norris et al. results in the formation of hydrazoic acid ($HN_3$) which is undesirable. Finally, the Norris et al. process consistently produces large crystals which may not be always preferred.

As an alternative to the Norris et al. process, U.S. Pat. No. 5,468,866 by Highsmith et al. describes another process for preparing bis-(1(2)H-tetrazol-5-yl)-amine monohydrate. A disadvantage noted by Highsmith et al. of the Norris et al. process is in purification of the final product wherein the hot reaction mixture is treated with concentrated hydrochloric acid and then cooled. Resultant entrapment of the sodium salt within the particles was attributed to this treatment step. The Highsmith et al. process involves reaction of a dicyanamide salt and an azide salt at high temperature in the presence of an acid reagent having a pKa in the range of from about 3 to about 9. The Highsmith et al. example with the highest yield called for the use of boric acid as the acid reagent which can lead to a co-precipitation problem with the BTAw product.

Despite previous processes of preparing bis-(1(2)H-tetrazol-5-yl)-amine monohydrate, further developments in the process have been sought by the present inventors.

SUMMARY OF THE INVENTION

In accordance with the purposes of the present invention, as embodied and broadly described herein, the present invention includes a process of preparing bis-(1(2)H-tetrazol-5-yl)-amine monohydrate including combining a dicyanamide salt, an azide salt and water to form a first reaction mixture, adding a solution of a first strong acid characterized as having a pKa of less than about 1 to said first reaction mixture over a period of time characterized as providing a controlled reaction rate so as to gradually form hydrazoic acid without loss of significant quantities of hydrazoic acid from the solution while heating the first reaction mixture at temperatures greater than about 65° C., heating the resultant reaction mixture at temperatures greater than about 65° C. for a period of time sufficient to substantially completely form a reaction product, treating the reaction product with a solution of a second strong acid to form a product of bis-(1(2)H-tetrazol-5-yl)-amine monohydrate, and, recovering the bis-(1(2)H-tetrazol-5-yl)-amine monohydrate product.

DETAILED DESCRIPTION

The present invention is concerned with the preparation of bis-(1(2)H-tetrazol-5-yl)-amine monohydrate (BTAw).

The preparation of bis-(1(2)H-tetrazol-5-yl)-amine monohydrate can be as follows. In the process of the present invention, a dicyanamide salt and an azide salt are reacted as a solution of a strong acid is gradually added. The reaction preferably takes place at a temperature in the range from about 65° C. up to reflux temperature. After the reaction is substantially complete, the reaction solution is treated with a solution of a second strong acid to form the product of BTAw, and the product is isolated, by filtering, treatment with a nitrite salt, drying, recrystallizing, and additional drying.

In contrast to prior art teachings, the dicyanamide salt is reacted with the azide salt with the gradual addition of a solution of a strong acid characterized as having a pKa of less than about 2, preferably less than about 1. Also, a strong acid, i.e., an acid with a pKa of <1 is added gradually over a period of time as opposed to a single addition of a weak acid, i.e., an acid with a pKa of >3. Also, the strong acid is preferably present in an amount of less than about 0.9 mole for each mole of the azide salt, preferably less than about 0.67 mole per mole of the azide salt.

The gradual addition of the solution of a strong acid occurs over a period of time characterized as providing a controlled reaction rate so as to gradually form hydrazoic acid without loss of significant quantities of hydrazoic acid from the solution. Generally, such periods of time can range from about 12 to 24 hours, although either longer or shorter periods may be used as well in some instances. By avoiding the loss of any significant hydrazoic acid from the solution as it is formed, the dicyanamide salt can be added in stoichiometric amounts for the amount of azide salt or in a slight excess, e.g., about 2.05 moles of azide salt per 1.00 mole of dicyanamide salt.

In addition, the strong acid should not participate or interfere with the reaction or the product recovery, that is, it should not react with the azide salt or dicyanamide salt under the reaction conditions and should remain soluble during both the reaction and recovery stages of the process. Suitable inorganic acids can be used and can be chosen from among hydrochloric acid (HCl), sulfuric acid ($H_2SO_4$), phosphoric acid ($H_3PO_4$), nitric acid ($HNO_3$), perchloric acid ($HClO_4$), and mixtures thereof. Hydrochloric acid is most preferred as the strong acid. Suitable organic acids such as trifluoroacetic acid, trifluoromethane sulfonic acid, methane sulfonic acid and the like may be used as well. In addition, a salt of hydrogen sulfate may be used as well.

Organic and inorganic salts of dicyanamide may be used. Typical salts include the silver, cadmium, copper, iron, zinc, magnesium, calcium, sodium, potassium, cesium dicyanamide salts, and mixtures thereof. The alkali and alkaline earth dicyanamide salts are preferred with sodium dicyanamide being most preferred.

Inorganic salts of azide may be used. Typical salts include silver (Ag), cadmium (Cd), copper (Cu), iron (Fe), zinc (Zn), magnesium (Mg), calcium (Ca), sodium (Na) and potassium (K) azide salts, and mixtures thereof. The alkali and alkaline earth azide salts are preferred with sodium azide being most preferred.

The reaction solution is heated to a temperature greater than 65° C., and preferably at reflux temperature. The reflux temperature will vary depending on the ingredient concentrations and upon the local elevation or barometric pressure. The reflux temperature will generally be greater than about 95° C. It is possible to increase the reflux temperature by applying pressure to the reaction. The reaction ingredients may be combined either prior to or during the heating step.

Several variations of the acidification step are possible. A solution of a strong acid can be introduced into the reaction solution by direct addition or the reaction solution may be introduced into a solution of a strong acid by indirect addition. In addition, the temperature of the reaction solution and acid may also vary. The reaction solution is treated with a strong acid to fully convert any sodium salt to the protonated product. Taking the solution to a low pH also dramatically improves purity by reducing the presence of salt impurities. The strong acid used to treat the reaction solution preferably has a pKa <2. Inorganic and organic acids may be used in the acidification step. Currently preferred strong acids include HCl, $H_2SO_4$, $H_3PO_4$, $HNO_3$, $HClO_4$, and mixtures thereof with HCl being most preferred.

After acidification, the precipitated particles are isolated. Conventional particle separation techniques may be used such as centrifugation, filtration, and ultrafiltration, with filtration and washing being currently preferred. Washing removes acid and soluble by-products.

The present invention yields substantially pure BTAw suitable for its further use without the need for major purification efforts as required by Norris et al. Minor purification can be accomplished using conventional techniques, such as recrystallization from hot water or other suitable solvents.

The present invention is more particularly described in the following examples which are intended as illustrative only, since numerous modifications and variations will be apparent to those skilled in the art.

EXAMPLE 1

To a 2 liter three-neck reaction flask containing 67.2 grams (g) of sodium dicyanamide (0.755 mole) and 103 g of sodium azide (1.59 mole) was added 400 milliliters (mL) of water. The solution mixture was heated to gentle reflux with stirring. The initial pH of the solution mixture was approximately 10. Using a diaphragm pump, 650 mL of 1.6 M aqueous HCl was injected into the refluxing solution mixture over the course of 24 hours. This rate of addition calculates to 0.45 ml of hydrochloric acid (0.72 millimole) per minute, or a total amount of 1.04 moles of acid. The pH of the solution mixture decreased to 6.5 after addition of all of the HCl. After the addition, the solution mixture was allowed to continue reaction under gentle reflux for another 24 hours. The reaction was then stopped, cooled and the resulting slurry was treated with 0.45 liter (L) of 4M HCl to convert the sodium salt of bis-(1(2)H-tetrazol-5-yl)-amine to the free acid. This mixture was filtered and the filtrate treated with 0.5 moles of sodium nitrite to destroy any residual azides. The crude white precipitate was dried in a vacuum oven at 65° C. overnight. The crude yield was 136.3 g. The crude material was recrystallized from 6 L of boiling water that was treated with 20 mL of concentrated HCl to give 110.5 g (85.6% yield) of white, amorphous of bis-(1(2)H-tetrazol-5-yl)-amine monohydrate (BTAw). The product had the appropriate purity for low-smoke pyrotechnic applications.

Although the present invention has been described with reference to specific details, it is not intended that such details should be regarded as limitations upon the scope of the invention, except as and to the extent that they are included in the accompanying claims.

What is claimed is:

1. A process of preparing of bis-(1(2)H-tetrazol-5-yl)-amine monohydrate comprising:

combining a dicyanamide salt, an azide salt and water to form a first reaction mixture;

adding a solution of a first acid characterized as having a pKa of less than about 2 to said first reaction mixture over a period of time wherein a controlled reaction rate is provided so as to gradually form hydrazoic acid without loss of significant quantities of hydrazoic acid from the solution while heating the first reaction mixture at temperatures greater than about 65° C.;

heating the resultant reaction mixture at temperatures greater than about 65° C. for a period of time sufficient to substantially completely form a reaction product;

treating the reaction product with a solution of a second acid to form a product of bis-(1(2)H-tetrazol-5-yl)-amine monohydrate; and, recovering the bis-(1(2)H-tetrazol-5-yl)-amine monohydrate.

2. The process of claim 1 wherein said first acid is characterized as having a pKa of less than about 1.

3. The process of claim 1 wherein said temperatures are reflux temperatures.

4. The process of claim 1 wherein said first acid is selected from the group consisting of HCl, $H_2SO_4$, $HNO_3$, $H_3PO_4$, $HClO_4$, trifluoroacetic acid, trifluoromethane sulfonic acid, methane sulfonic acid and mixtures thereof.

5. The process of claim 1 wherein said first acid is selected from the group consisting of HCl, $H_2SO_4$, $HNO_3$, $H_3PO_4$, $HClO_4$ and mixtures thereof.

6. The process of claim 1 wherein said first acid is HCl.

7. The process of claim 1 wherein about 0.65 moles of said first acid is added for each mole of azide salt.

8. The process of claim 1 wherein said azide salt is sodium azide.

9. The process of claim 1 wherein said dicyanamide salt is sodium dicyanamide.

10. The process of claim 1 wherein said dicyanamide salt is sodium dicyanamide, said azide salt is sodium azide, and said first acid is HCl.

11. The process of claim 1 wherein the mole ratio of azide salt to dycyanamide salt is at least about 2.05 to 1.

12. The process of claim 1 wherein the mole ratio of azide salt to dycyanamide salt is about 2.05 to 1.

\* \* \* \* \*